United States Patent
Laugharn, Jr. et al.

(10) Patent No.: US 11,579,143 B2
(45) Date of Patent: Feb. 14, 2023

(54) ACOUSTIC BASED CELL SEPARATION

(71) Applicant: Covaris, LLC, Woburn, MA (US)

(72) Inventors: James A. Laugharn, Jr., Boston, MA (US); Carl Beckett, Harvard, MA (US); Srikanth Kakumanu, Chelmsford, MA (US)

(73) Assignee: Covaris, LLC, Woburn, MA (US)

( * ) Notice: Subject to any disclaimer, the term of this patent is extended or adjusted under 35 U.S.C. 154(b) by 938 days.

(21) Appl. No.: 16/419,057

(22) Filed: May 22, 2019

(65) Prior Publication Data

US 2019/0361008 A1    Nov. 28, 2019

Related U.S. Application Data

(60) Provisional application No. 62/675,427, filed on May 23, 2018.

(51) Int. Cl.
| | | |
|---|---|---|
| *G01N 33/50* | (2006.01) | |
| *B01L 3/00* | (2006.01) | |
| *G01N 15/14* | (2006.01) | |

(52) U.S. Cl.
CPC .... *G01N 33/5094* (2013.01); *B01L 3/502761* (2013.01); *G01N 15/1404* (2013.01); *B01L 2200/0636* (2013.01); *B01L 2200/0652* (2013.01); *B01L 2200/10* (2013.01); *B01L 2300/0864* (2013.01); *B01L 2400/0436* (2013.01); *G01N 2015/142* (2013.01)

(58) Field of Classification Search
CPC ......... G01N 15/1404; G01N 2015/142; G01N 33/5094; B01L 3/502761; B01L 2200/0636; B01L 2200/0652; B01L 2200/10; B01L 2300/0864; B01L 2400/0436

See application file for complete search history.

(56) References Cited

U.S. PATENT DOCUMENTS

| | | |
|---|---|---|
| 8,592,204 B2 | 11/2013 | Lipkens et al. |
| 8,691,145 B2 | 4/2014 | Dionne et al. |
| D722,674 S | 2/2015 | Lipkens et al. |
| 9,011,699 B2 | 4/2015 | Dionne et al. |
| 9,320,995 B2 | 4/2016 | Laugharn, Jr. et al. |
| 9,421,553 B2 | 8/2016 | Dionne et al. |
| 9,636,609 B2 | 5/2017 | Curran et al. |
| 2003/0108954 A1* | 6/2003 | Mutz ...................... C12M 33/00 435/325 |
| 2012/0160746 A1* | 6/2012 | Thorslund .............. C12M 47/04 209/552 |
| 2013/0264271 A1 | 10/2013 | Yoshioka et al. |
| 2013/0277316 A1 | 10/2013 | Dutra et al. |
| 2013/0284271 A1 | 10/2013 | Lipkens et al. |
| 2016/0008532 A1* | 1/2016 | Fiering ............... A61M 1/3693 210/666 |

OTHER PUBLICATIONS

Muller et al., Ultrasound-induced acoustophoretic motion of microparticles in three dimensions. J Phys Rev E. Mar. 1, 2013; 13 pages.

* cited by examiner

*Primary Examiner* — Brian J. Sines

(74) *Attorney, Agent, or Firm* — Wolf, Greenfield & Sacks, P.C.

(57) ABSTRACT

Apparatus and method for separating whole cells from a mixture, e.g., including liquid, other cell types, nucleic acid material, or other components. Focused acoustic energy may be used to move whole cells in a chamber so that the cells exit the chamber via a first outlet rather than a second outlet. A filter may, or need not, be used to assist in separation.

22 Claims, 5 Drawing Sheets

ACOUSTIC BASED CELL SEPARATION

RELATED APPLICATION

This application claims priority under 35 U.S.C. § 119(e) to U.S. Provisional Application Ser. No. 62/675,427, entitled "ACOUSTIC BASED CELL SEPARATION" filed May 23, 2018, which is herein incorporated by reference in its entirety.

BACKGROUND

1. Field of Invention

Methods and apparatus for separating cells from fluid or other materials, e.g., using focused acoustic energy to move cells relative to each other or relative to other materials.

2. Related Art

Various techniques are known for separating materials, such as biological cells from a liquid containing other components. For example, cells may be separated from a liquid using filters, centrifugation, etc.

SUMMARY OF INVENTION

Separation of cells from a mixture containing the cells, a liquid such as water, and other materials can be useful in a variety of different processes and for different reasons. For example, certain cancer tumors in the human body release cancerous cells that circulate in the blood, and thus are called circulating tumor cells (CTCs). This allows cancers to be identified and diagnosed by analyzing a blood sample alone, thus avoiding other more costly techniques such as body scans using magnetic resonance imaging (MRI) or other systems. However, concentrations of CTCs in whole blood are low, i.e., the ratio of CTCs to normal white blood cells (WBC) may be 1:10,000 or less, potentially making identification of CTCs difficult. Techniques described herein that use acoustic energy-based separation may take advantage of the differential cell sizes (diameter) and possibly densities to separate CTCs from other blood cells and blood contents, e.g., since CTCs may be larger than normal WBC and other blood cells. This allows the effective separation of CTCs from other blood cells in relatively rapid and low cost manner.

Other applications to which systems and processes described herein may be put to use include separation of viral particles and sepsis-causing bacterial or fungal cells from the contents of whole blood. In the case of certain viral infections and/or sepsis infections, the number of viral particles or sepsis-causing bacteria or fungi cells in a typical blood sample may be very small. Techniques according to inventive aspects allow for the separation of viral particles from other blood contents, e.g., by separating red blood cells, white blood cells and/or other cells from whole blood which leaves sought-for viral particles and/or sepsis bacteria or fungi in liquid material separated from the cells. This increases the concentration of such viral particles, bacteria or fungi to higher values, allowing for the more effective isolation of these components for analysis.

In one aspect of the invention, a method is provided for separating cells from a liquid mixture, such as whole blood. The method may include providing a plurality of whole cells in a mixture containing liquid into a chamber via an inlet of the chamber. For example, whole blood may be pumped into a cylindrical chamber either in undiluted form, or after dilution of the blood with water or other liquid so as to provide the mixture having a suitable cell concentration, e.g., of 3% or less. Focused acoustic energy may be transmitted into the chamber, e.g., to create a line-shaped focal zone of acoustic energy in the chamber so as to expose the plurality of whole cells in the mixture to acoustic energy at the line-shaped focal zone. The acoustic energy may be transmitted by an acoustic energy source so that the chamber is absent of any standing acoustic waves. Standing acoustic waves have been employed for separation of cells from other cells in a sample, but while some embodiments herein could be combined with the use of standing waves, other embodiments herein do not use standing waves to separate cells from a mixture. The plurality of whole cells in the chamber may be moved using at least in part the focused acoustic energy so the plurality of whole cells exit the chamber via a first outlet rather than a second outlet. That is, a mixture containing the plurality of cells may be introduced into the chamber, and focused acoustic energy may be used to move the plurality of cells to exit from a first outlet of the chamber rather than a second outlet. The plurality of whole cells may be removed from the chamber via the first outlet, and liquid portion of the mixture may be removed from the chamber via the second outlet. The liquid removed from the chamber via the second outlet may contain other cells and/or materials that are different from the plurality of cells removed via the first outlet. For example, it may be desired to separate white blood cells from a mixture containing white blood cells, viral particles and bacteria. White blood cells may be moved by focused acoustic energy to exit the chamber via the first outlet so that viral particles and bacteria exit the chamber via the second outlet. This may allow for the identification and analysis of viral particles and/or bacteria separate from the white blood cells. Moreover, the liquid mixture containing viral particles and bacteria may be treated with a similar focused acoustic energy separation process that separates bacterial cells from the viral particles. This may allow for the separation of bacteria from smaller viral particles, free DNA and other nucleic acid material, and so on.

In some embodiments, the chamber may include a filter that flowwise separates a first portion of the chamber that is in fluid communication with the inlet and the first outlet and a second portion of the chamber that is in fluid communication with the second outlet. Thus, the filter may be arranged such that liquid that enters the chamber at the inlet must pass through the filter to exit the chamber via the second outlet. The filter may help separate the plurality of cells from other components of the mixture, e.g., because the cells may be too large to pass through the pores or other openings of the filter but other components may pass through. For example, the filter may be arranged such that each whole cell in the plurality of whole cells is too large to pass through the filter and so the whole cells cannot flow through the filter to the second outlet. In some embodiments, the filter has an area of at least 2000 square mm, and in some cases the focused acoustic energy may operate to move the plurality of whole cells in a direction away from the filter. Such movement may be done by avoiding vibrating or otherwise moving the filter to dislodge cells from the filter, but instead may involve "pushing" the cells away from the filter. This may help keep the filter from clogging while also avoiding lysing or other disruption of the cells.

In some embodiments, the chamber includes a first end where the inlet is located that is opposite a second end where the first and second outlets are located, and a filter may extend in a direction from the first end to the second end. For example, the chamber may have a cylindrical shape with the inlet at a first end and the first and second outlets at a second end. The filter may extend from the first end to the second end along the cylinder. The focused acoustic energy may be transmitted into the chamber between the first and second ends so that the line-shaped focal zone is arranged in a direction from the first end to the second end. In some cases, the line-shaped focal zone may be located above the filter, and may have a length of 75 mm, and a frequency of 0.25 to 2.5 MHz. The plurality of whole cells may flow within the chamber in a direction along the line-shaped focal zone, e.g., the line-shaped focal zone may extend from the inlet toward the first and second outlets.

Whole cells that are separated may be undamaged by the separation process in the chamber. For example, the plurality of whole cells may be viable when introduced into the chamber via the inlet and remain viable after being removed from the chamber via the first outlet. This may be particularly useful if separated cells are to be cultured or analyzed while alive after the separation process. The whole cells may have any suitable concentration when introduced into the separation chamber, e.g., have a concentration of near zero to 50% in the mixture at the inlet, and may be introduced at any suitable flow rate, e.g., at a flow rate of 1 milliliter per minute to 1000 milliliters per minute or more.

It should be noted that the chamber need not include a filter and cells may be separated in the chamber and directed to exit via the first outlet without the use of a filter or similar structure. In one embodiment, a cell separation chamber includes the inlet at a first end of the chamber and the first and second outlets are arranged at a second end of the chamber opposite the first end. Flow of mixture from the inlet to the first and second outlets may be horizontal, and the first outlet may be positioned below the second outlet. Alternately, flow from the inlet to the first and second outlets may be vertical and the inlet may be located above the first and second outlets. The focused acoustic energy may enter the chamber along a first side of the chamber, and the first outlet may be arranged nearer the first side than the second outlet. That is, the plurality of cells may be moved within the chamber to exit the chamber via the first outlet even though the first outlet is arranged nearer the side of the chamber where the acoustic energy is transmitted into the chamber. This may be achieved because the acoustic energy causes cells to initially move away from the first side of the chamber, but then flow back along the chamber wall toward the first side for collection near the first side of the chamber. Collection of cells along the first side allows the cells to exit via the first outlet, which is adjacent the first side of the chamber. In some cases, gravity may assist in moving cells to the first outlet.

In another embodiment, the inlet and the first outlet of the chamber may be located at a first end of the chamber and the second outlet may be arranged at a second end of the chamber opposite the first end. For example, flow from the inlet to the second outlet may be vertical and the inlet may be located below the second outlet. Focused acoustic energy may enter the chamber along a first side of the chamber, and the first outlet may be arranged nearer the first side than the inlet. The plurality of whole cells may be moved at least in part to the first outlet by gravity, e.g., the cells may collect on the first side of the chamber and fall in the chamber by gravity to the first outlet.

In another aspect of the invention, an apparatus for separating cells from a liquid mixture includes a chamber having an inlet arranged to introduce the liquid mixture including a plurality of whole cells into the chamber, and first and second outlets. An acoustic energy source may be arranged to transmit focused acoustic energy toward the chamber to form a focal zone of acoustic energy in the chamber. The focal zone of acoustic energy, which may be line-shaped and extend along a flow path of cells, may be arranged to move the plurality of whole cells in the chamber at least in part so the plurality of whole cells exit the chamber via a first outlet rather than a second outlet. A coupling medium, such as a liquid or solid or other material, may be arranged to transmit the focused acoustic energy from the acoustic energy source to the chamber. Thus, the acoustic energy source may be located outside of the chamber and transmit acoustic energy into the chamber.

In one embodiment, the chamber includes a filter that flowwise separates a first portion of the chamber that is in fluid communication with the inlet and the first outlet, and a second portion of the chamber that is in fluid communication with the second outlet. The filter may be arranged such that liquid that enters the chamber at the inlet must pass through the filter to exit the chamber via the second outlet. The acoustic energy source may be arranged to create the line-shaped focal zone in a location spaced from the filter, e.g., so as to push cells away from the filter, at least in initial movement. The chamber may include a first end where the inlet is located that is opposite a second end where the first and second outlets are located, and the filter may extend in a direction from the first end to the second end. The acoustic energy source may be arranged to create a line-shaped focal zone so as to extend in a direction from the first end to the second end, e.g., so that the plurality of cells flow in the chamber along the focal zone. In one embodiment, flow from the inlet to the first and second outlets is horizontal, but may be vertical.

In other embodiments, a filter need not be included and the chamber may include a first end where the inlet is located that is opposite a second end where the first and second outlets are located, and the inlet may be arranged to introduce the mixture into the chamber in a direction toward the second end. The chamber may be arranged such that flow from the inlet to the first and second outlets is horizontal, and the first outlet may be located below the second outlet at the second end of the chamber. In other cases, the chamber may be arranged such that flow from the inlet to the first and second outlets is vertical, and the inlet may be located above the first and second outlets. In another arrangement, the chamber may include a first end where the inlet and the first outlet are located that is opposite a second end where the second outlet is located, and the inlet may be arranged to introduce the mixture into the chamber in a direction toward the second end, e.g., upwardly in the chamber. Thus, the chamber may be arranged such that flow from the inlet to the second outlet is vertical, and the inlet may be located below the second outlet. The acoustic energy source may be arranged to transmit focused acoustic energy into the chamber along a first side of the chamber, and the first outlet may be arranged nearer the first side than the inlet.

In another aspect of the invention, an apparatus for separating cells from a liquid mixture includes a chamber including a plurality of whole cells into the chamber. Unlike embodiments above, the chamber need not include an inlet or outlet. An acoustic energy source may be arranged to transmit focused acoustic energy toward the chamber to form a focal zone of acoustic energy in the chamber. The focal zone of acoustic energy, which may be line-shaped, may be arranged to move the plurality of whole cells in the chamber at least in part so the plurality of whole cells accumulate in one portion of the chamber. In some embodiments, the cells may accumulate in a portion of the chamber that is adjacent to where acoustic energy is transmitted into the chamber by the acoustic energy source. A coupling medium, such as a liquid or solid or other material, may be arranged to transmit the focused acoustic energy from the acoustic energy source to the chamber. Thus, the acoustic energy source may be located outside of the chamber and transmit acoustic energy into the chamber.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

Figure 1:
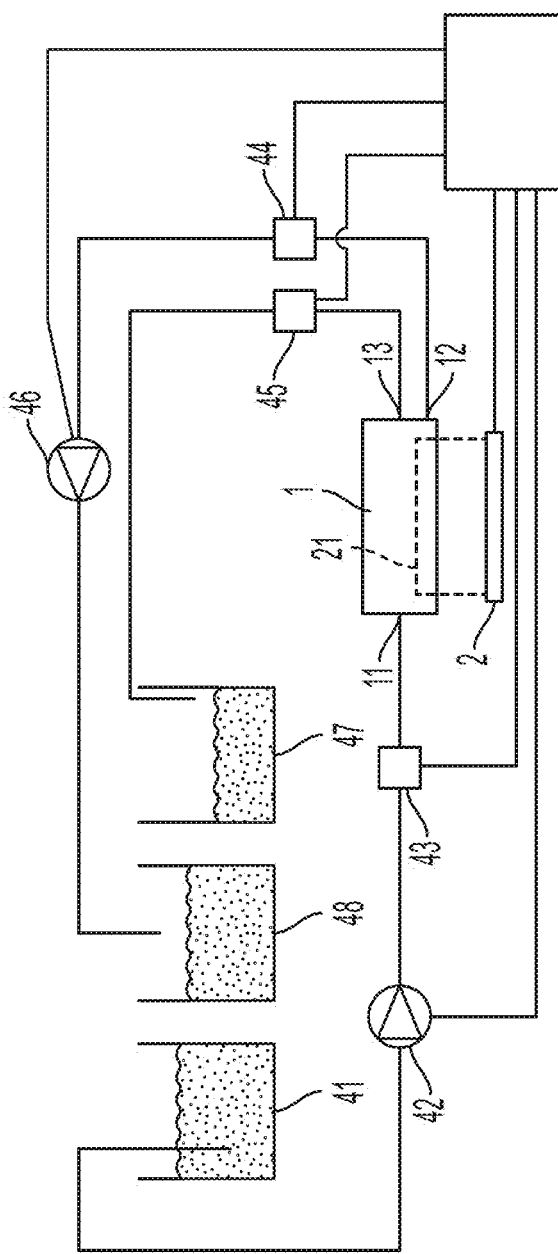
FIG. 1 is a schematic diagram of a cell separation system in an illustrative embodiment.

FIG. 1 shows a schematic diagram of a system arranged to separate cells in a liquid mixture. As discussed above, the mixture may include a plurality of only one type of cell, such as a plurality of the same type of yeast cells, that are to be separated from liquid in the mixture, or may include cells of two or more different types, such as blood cells and bacteria, that are to be separated from each other. As also discussed above, mixtures having two or more different cell types that are to be separated may be separated by selectively lysing cells of one type while leaving cells of another type to be isolated in whole form. This may allow for easier separating of the whole cells because the lysed cells are no longer in whole form. Generally, whole cells will be moved by focused acoustic energy in a separation chamber in different ways, e.g., moved at different speeds, than cells of other sizes or cellular material released from lysed cells. This can be exploited to separate cells from a liquid mixture, which may include cells of a different type.

The illustrative embodiment of FIG. 1 is just that—an illustrative embodiment and it should be understood that various modifications of the system may be made. In this embodiment, a mixture including a liquid and whole cells is held in a reservoir or tank 41 which may be of any suitable size, shape or configuration. For example, the tank 41 may contain less than a liter of mixture, or 10's or 100's of liters, may include a bulk stirring apparatus (such as a mixer) to keep cells suitably suspended or otherwise agitated, a heater or chiller to heat or cool the mixture, and so on. In this embodiment, the cells are at a 3% concentration by volume in the tank 41, but other concentrations may be employed, such as cell concentrations near zero to 50% by volume. The mixture may be pumped from the tank 41 by a pump 42, such as a peristaltic pump. The pump 42 may be selected for its capability to move cells in the mixture without damaging the cells, if desired. The pump 42 may be operated under the control of a control circuit 3 which may include various sensors, input/output devices, actuators, etc. as discussed in more detail below. For example, an input detector 43 may detect a cell concentration of the mixture entering a separation chamber 1, e.g., by optical or other turbidity measure of the mixture. Information from the detector 43 may be used to measure and control operation of the separation chamber 1.

The mixture enters the separation chamber 1 via an inlet 11 which is located at a first end of the chamber 1. At a second end of the chamber 1 opposite the first end, first and second outlets 12, 13 may be located for respectively removing portions of the mixture that are more rich and less rich in cells. That is, cells may generally exit the first outlet 12, while liquid that is generally free of cells may exit the second outlet 13. For ease of reference herein, cells are said to exit the first outlet 12, and to not exit the second outlet 13, but it should be understood that at least some cells that are desired to be directed for exit from the first outlet 12 may exit the second outlet 13. Also, if a mixture includes cells of two or more different types, cells of a first type may predominantly exit via the first outlet 12, while cells of other types may predominantly exit via the second outlet 13. Cells are delivered by a pump 46 to a collection reservoir or tank 48, and a detector 44 may detect a concentration of cells in the flow, e.g., to help control operation of the separation chamber 1. Liquid that is free or largely free of cells may be directed to a reservoir or tank 47, and a detector 45 may detect the presence of cells in the flow, again for use in system control. For example, the presence of cells exiting the second outlet 13 may indicate a need to make some adjustment to system operation, whether in cell concentration in the tank 41, a flow rate of the mixture, or other parameters. In some experiments performed by the inventors, a mixture of yeast cells having a concentration of about 3% by volume was provided to the inlet 11 of a separation chamber 1 at a flow rate of about 20 milliliters per minute, with flow rates out of the first and second outlets 12, 13 at about 10 milliliters per minute each. Of course, other flow rates and concentrations may be employed in other embodiments.

Figure 2:
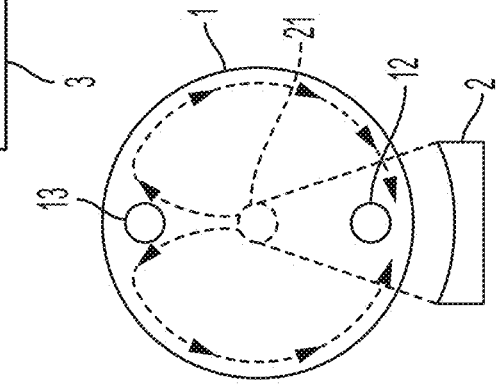
FIG. 2 shows a perspective view of a separation chamber in the illustrative embodiment of FIG. 2.

As will be described in detail below cells are separated in the chamber 1 by focused acoustic energy that is transmitted into the chamber 1 by an acoustic energy source 2, such as a piezoelectric acoustic transducer operating under the control of the control circuitry 3. As shown in FIG. 2, the focused acoustic energy may generate a focal zone 21 of acoustic energy having a line or extended rod-like shape that extends along a length of the chamber and/or along a flow path of the mixture through the chamber 1. Systems that create a line-shaped focal zone are known in the art, and L-series focused acoustic systems sold by Covaris, Inc. of Woburn, Mass. are suitable for use in this application. Aspects of the invention are not limited to use with line-shaped focal zones however, and point, spherical or capsule-shaped focal zones may be used as well. In some cases, a plurality of focal zones of any suitable shape may be used, e.g., multiple point or capsule-shaped focal zones may be employed in the chamber 1 of FIG. 1, e.g., where the focal zones are arranged along a line. The internal shape of the chamber 1 may be configured to operate with a focal zone of a particular shape, e.g., a cylindrically shaped chamber 1 has been found useful with a line-shaped focal zone, and a spherical chamber 1 may be useful with a point or spherically shaped focal zone. Acoustic energy emitted by the acoustic source may travel through a coupling medium, such as water, an elastomer, or other material to the chamber 1. Thus, as can be seen in FIG. 2, the acoustic source 2 is located outside of the chamber 1 so focused acoustic energy can be transmitted to, and through, the chamber 1 wall. Acoustic energy parameters or settings for the acoustic energy source 2 may be set and/or adjusted as suitable for each particular application. In embodiments involving separation of yeast and white blood cells, a Covaris L-type system was set to operate at peak incident power (PIP) between 25 to 300 PIP, a duty cycle of 20-50%, and a cycles per burst (CPB) of 500-2000 CPB. In this illustrative embodiment, the first outlet 12 through which cells exit the chamber 1 is located adjacent a side of the chamber 1 through which acoustic energy is transmitted into the chamber 1. This is counterintuitive in some sense because acoustic energy may be believed to "push" cells or other material in the direction of propagation of the acoustic energy, e.g., upward in the chamber in FIG. 1. This aspect of the invention is exploited to separate cells in a highly efficient manner.

Figure 3:
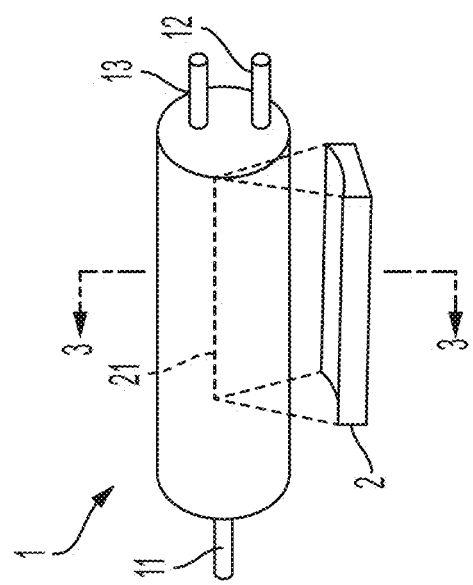
FIG. 3 shows a cross sectional view of the separation chamber the line 3-3 in FIG. 2.

FIG. 3 shows a cross sectional view of the chamber 1 and acoustic energy source 2 along the line 3-3 in FIG. 2. The location of the focal zone 21 is inward from the chamber 1 walls and may be near the geometric center of the cross section of the chamber 1. The focal zone 21 generates a flow of cells as shown in dashed line in FIG. 3 such that cells flow upwardly away from the focal zone 21 and into contact with the chamber 1 wall near an upper portion of the chamber 1. The cells then tend to flow along the chamber wall outwardly and downwardly toward a bottom of the chamber 1. Near the bottom of the chamber 1, the cells tend to accumulate since there is little force exerted by the acoustic energy to cause the cells to flow upwardly. As a result, the cells tend to collect at a bottom of the chamber 1, and because of the flow of mixture from the first end at the inlet 11 to the second end at the first and second outlets 12, 13, the cells tend to flow horizontally along the chamber 1 to the first outlet 12. Cell-free liquid, or liquid having fewer cells of interest, exits the second outlet 13. While in this embodiment the chamber 1 interior is cylindrical and generally featureless, structure may be provided in the chamber 1 interior to help direct flow in a desired way. For example, baffles or other structures may be used to help direct flow of cells toward the first outlet 12 if desired. In some embodiments, the chamber 1 may be inclined relative to the horizontal, e.g., 1 to 20 degrees or more, so that cells that accumulate on a bottom of the chamber 1 tend to flow by the force of gravity toward the first outlet 12.

Figure 4:
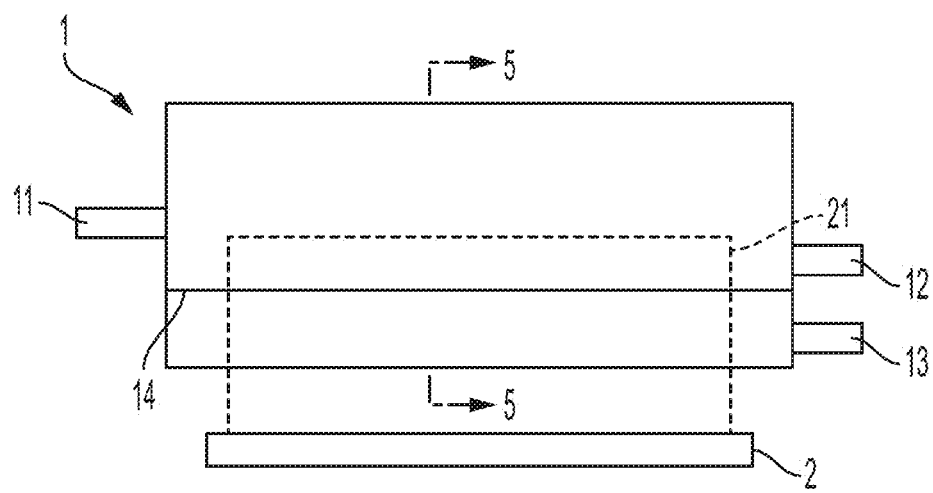
FIG. 4 shows a schematic diagram of a separation chamber in another illustrative embodiment including a filter.
Figure 5:
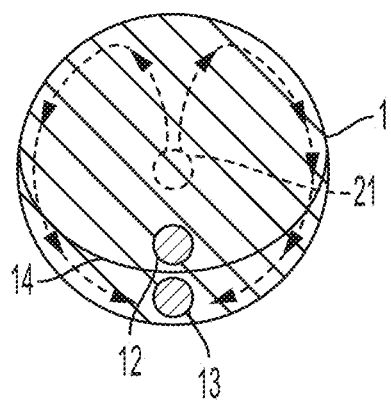
FIG. 5 shows a cross sectional view of the separation chamber the line 5-5 in FIG. 4.

In some embodiments, the chamber may include a filter or other structure that helps separate cells from liquid in the mixture. For example, FIG. 4 shows an embodiment in which a chamber 1 includes a filter 14 that is arranged in the chamber 1 so that liquid that flows from the inlet 11 to the second outlet 13 must pass through the filter 14. The filter 14 is arranged so that cells having a size to be separated from other components of the mixture are too large to flow through the filter 14. As a result, the cells may accumulate on a top of the filter 14 and flow out of the first outlet 12. FIG. 5 shows a cross sectional view of the chamber 1, and illustrates how the acoustic energy source 2 creates a focal zone 21 that is above the filter 14. Mixture including cells enters the chamber 1 via the inlet 11 and flows generally along the filter 14 and, for example, a line-shaped focal zone 21 toward the first and second outlets 12, 13. The focal zone 21 causes flow of cells upward toward a top of the chamber and then outwardly in clockwise and counterclockwise directions along the outer wall of the chamber 1. Since the cells to be separated are too large to pass through the filter 14, the cells collect on a top of the filter 14 and flow toward a center portion of the filter 14. The cells that collect on the filter 14 flow toward and exit the chamber 1 via the first outlet 12. Liquid and other materials that pass through the filter 14 exit the chamber 1 via the second outlet 13. Unlike the FIG. 1 embodiment, in this embodiment of FIGS. 4 and 5, the first outlet 12 is not positioned adjacent a side of the chamber 1 where acoustic energy is transmitted into the chamber 1. Instead, the first outlet 12 is positioned adjacent the filter 14 at one end of the chamber 1 so cells collected on the filter 14 can flow into the first outlet 12. As shown in FIG. 5, the filter 14 may be sloped toward a center of the chamber 1 so that cells tend to flow toward a center of the filter for exit at the first outlet 12 which is positioned adjacent a center of the filter 14. Other arrangements are possible, though, such as having the filter 14 arranged in a V-shape in the cross sectional view of FIG. 5 with the first outlet 12 located adjacent a bottom of the V-shape to receive cells, or having the filter 14 sloped toward one side of the chamber 1 near the chamber wall and the first outlet 12 located to receive cells at a location near the chamber wall.

Figure 6:
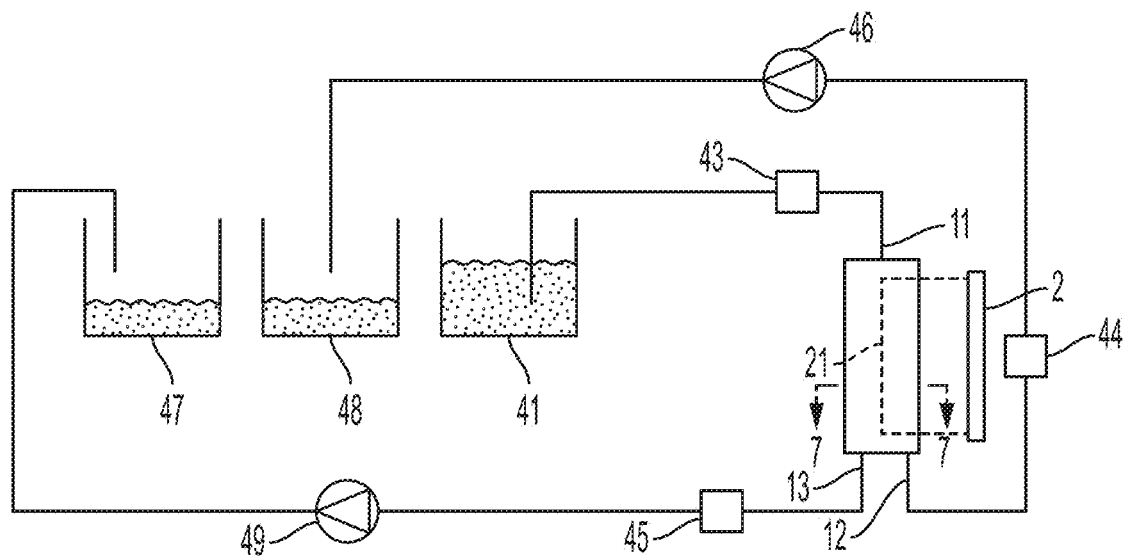
FIG. 6 is a schematic diagram of a cell separation system in an illustrative embodiment in which a separation chamber is oriented for vertical flow.

Although the embodiments in FIGS. 1 and 4 illustrate cell separation chambers arranged horizontally so flow through the chamber from the inlet to the first or second outlet is horizontal, a separation chamber may be arranged in other ways relative to gravity. For example, a chamber 1 may be arranged vertically as shown in FIG. 6. In this illustrative embodiment, a mixture from a tank 41 may be provided into an inlet 11 of a chamber that is arranged at an uppermost first end of the chamber 1. Flow through the chamber may be downwardly from the inlet 11 to the first and second outlets 12, 13 located at a lowermost second end of the chamber 1. An acoustic energy source 2 may be configured to transmit focused acoustic energy into the chamber 1 from a right side of the chamber 1 as shown in FIG. 6. As in the FIGS. 1 and 4 embodiments, the acoustic energy source 2 may create a line-shaped focal zone 21 that extends along a length of the chamber 1, but other focal zone arrangements are possible including one or more point, spherical or capsule-shaped focal zones. As shown in the cross-sectional view of FIG. 7, the focal zone 21 may be located away from the walls of the chamber 1, and near a center of the chamber as viewed in the cross section of FIG. 7. The focused acoustic energy at the focal zone 21 may be arranged to cause flow of cells in the mixture to move toward the left in FIG. 7, and then flow upwardly and downwardly in clockwise and counterclockwise directions as viewed in FIG. 7 along the chamber wall to a right side of the chamber 1. Cells may gather along a right side of the chamber 1, i.e., on a side nearest the acoustic energy source 2 and where acoustic energy is transmitted into the chamber 1. In some cases, cells may agglomerate on the chamber wall on the right side of the chamber 1 until a certain number of cells are clumped together, and then the cells may slough off or otherwise detach from the chamber wall and fall towards the first outlet 12. Alternately, the cells may gather on the right side of the chamber and fall toward the first outlet 12 under the force of gravity in a more random or continuous manner.

Figure 7:
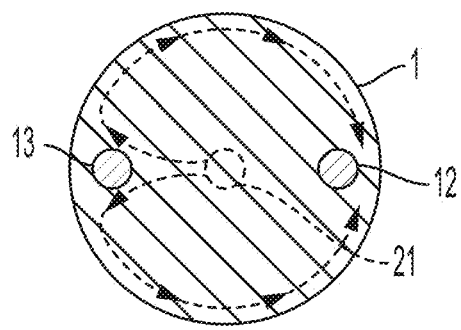
FIG. 7 shows a cross sectional view of the separation chamber along the line 7-7 in FIG. 6.

Note that a separation chamber 1 may be arranged with no inlet or outlet, and yet still function to separate cells from a mixture. For example, a chamber 1 may be arranged like that in FIGS. 6 and 7, but rather than having an inlet or outlet, a mixture containing cells may be poured or otherwise provided into the chamber 1. Focused acoustic energy may be introduced into the chamber in a way like that shown in FIGS. 6 and 7, so that cells flow as shown in FIG. 7 and accumulate in one portion of the chamber 1, e.g., at a side of the chamber 1 where acoustic energy is transmitted into the chamber 1. This may effectively separate cells from the mixture, e.g., cells that accumulate on one side may fall to a bottom of the chamber 1 on one side of the chamber 1 for later collection. In some cases, the chamber 1 may include a pocket or collection area at a bottom of the chamber so that cells which accumulate at a side of the chamber 1 fall into the pocket. This may help keep the cells in a local area for later collection, e.g., by pipette or similar device.

Flow through the chamber 1 may be driven by pumps 46 and 49 which draw fluid from the chamber 1, thereby drawing mixture from the tank 41 and to the chamber 1. The pumps 42, 46 need not operate continuously and may be activated as desired to achieve cell separation. For example, the pump 49 may be operated continuously for a period of time, such as 5 to 15 minutes while the pump 46 is inactive and there is no flow out of the first outlet 12. This may circulate cells from the tank 41 through the chamber 1 and to the tank 47. If desired, tanks 41 and 47 may be fluidly coupled to allow for cells to be recirculated. While the pump 49 is operated, the acoustic energy source 2 may be operated so that cells accumulate on a right side of the chamber 1. After the period of time, the pump 49 may stop operation and the pump 46 may be operated, e.g., for a minute or two, to remove accumulated cells from the chamber 1 to the tank 48. Thereafter, the pump 42 may be stopped and pump 49 again operated to circulate cells through the chamber 1 while the acoustic energy source 2 operates. Sensors may detect turbidity or other indications of cell concentrations in flow lines into, and out of, the chamber, and as discussed above, sensor information may be used to control the pumps 42, 46 and/or the acoustic energy source 2.

Figure 8:
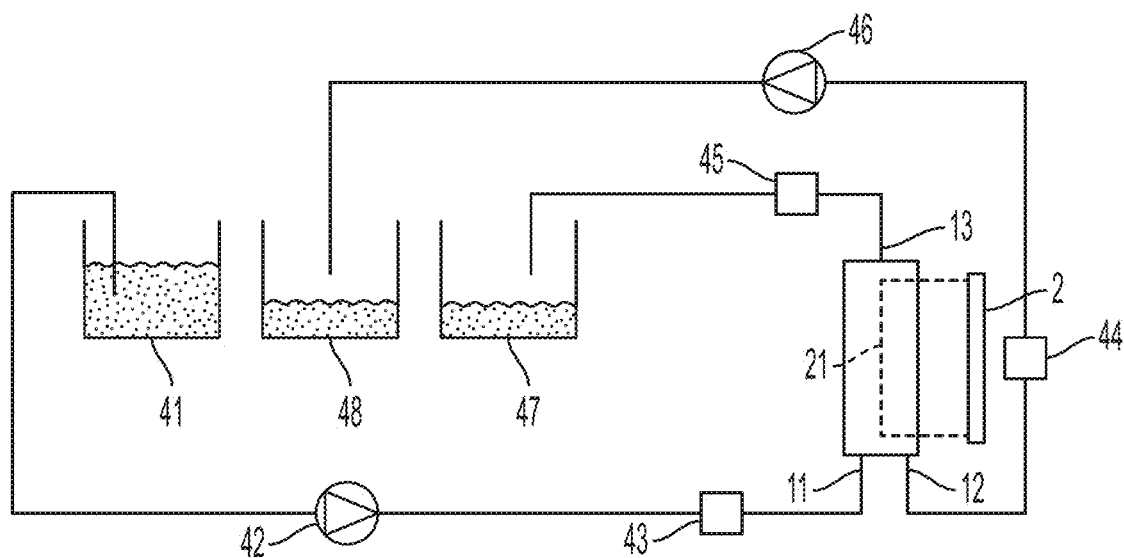
FIG. 8 is a schematic diagram of a cell separation system in another illustrative embodiment in which a separation chamber is oriented for vertical flow and from which cells exit the chamber at a lower end of the chamber.

A separation chamber arranged vertically is not limited to flow in which a mixture is introduced into the chamber from an upper area or portion of the chamber 1. Instead, a cell-containing mixture may be introduced from a lower area or portion of the chamber 1 as shown in FIG. 8. Liquid and cells in the mixture may flow upwardly in the chamber from the inlet 11 toward the second outlet 13, and the acoustic energy source 2 may transmit focused acoustic energy into the chamber 1 in the same way as in FIG. 6 so as to cause cells to flow outwardly and along the chamber wall to the right side of the chamber 1 as shown in FIG. 7. As in the FIG. 6 embodiment, cells may fall under the force of gravity at least in part to the first outlet 12 to exit the chamber 1. Liquid and other materials in the mixture may flow upwardly and exit the chamber 1 via the second outlet 13. Pumps may be used to drive flow through the chamber 1, and in this embodiment a pump 42 is arranged to deliver cell-containing mixture to the chamber 1 from a tank 41, and a pump 46 is arranged to pump separated cells from the chamber 1 to a tank 48. As in the FIG. 6 embodiment, the tanks 41 and 47 may be fluidly coupled or merged into a single tank to allow circulation of cell-containing liquid mixture through the chamber 1 and accumulation of cells in the chamber 1 (on the right side of the chamber 1). The pump 46 may be periodically, or continuously, operated to remove accumulated cells from the chamber 1, during which the pump 42 may be stopped. Other pumping arrangements may be used in this and other embodiments, and one or more sensors may be used to detect the presence of cells, including a concentration of cells in a flow to and/or from the chamber 1.

In one experiment employing a system like that in FIG. 8 but having tanks 41 and 47 merged into a single tank, a 1000 milliliter mixture including yeast cells at a concentration of 3.6% was supplied from a tank 41 to the chamber 1 via a peristaltic pump 42 that was operated for three 15 minute periods of time each at a flow rate of 10 milliliters per minute. A peristaltic pump 46 was not operated during the 15 minute periods of time while cells accumulated in the chamber 1, but after each 15 minute period, the pump 46 was operated for 3 minutes to remove 60 milliliters of liquid with accumulated cells from the chamber 1. The acoustic energy source 2, in this case an L-series Covaris machine, was operated at 100 PIP, 50% duty cycle, and 1000 CPB during each 15 minute period of time but not operated during the 3 minute cell removal cycles. After three circulation and cell removal cycles, the 180 milliliters of accumulated cell mixture in the tank 48 was analyzed using spectrophotometry at OD660, and it was found that the concentration of yeast cells in the tank 48 was at least 60% or 20 times greater than the starting material in the tank 41.

As described above, methods and systems described herein may be used in various separation processes and for different purposes. For example, circulating tumor cells (CTCs) in a blood sample may be separated from white blood cells (WBC) to increase the sensitivity of the non-hematologic cancer diagnostic assays (such as qPCR, next generation sequencing (NGS), MALDI-TOF of peptides/proteins, etc.) as well as for in vitro proliferation/culturing of purified CTCs. Concentrations of CTCs in whole blood are low, i.e., the ratio of CTC to normal WBC is unfavorable for downstream detection based on DNA, RNA or protein biomarkers. Enrichment of CTCs can be essential or at least beneficial to reduce interference due to the very high ratio of background biomolecules from normal cells versus those from CTCs (e.g., ratios are usually greater than 10,000 to 1 depending state and type of cancer). Focused acoustic energy separation described herein may take advantage of the differential cell sizes (diameter) and possibly densities of CTCs and WBCs, since CTCs are larger than normal WBC and other blood cells. In one illustrative separation process for isolating or concentrating CTCs, red blood cells may first be hematolyzed using chemical or osmotic lysis and then the remaining cells in the mixture (e.g., CTCs and WBCs) may be subjected to a focused acoustic energy separation like that described above to separate WBCs from CTCs. Separation has previously been done using a standing acoustic wave that is based on trapping cells in a certain area of the standing wave. However, using standing acoustic waves requires relative homogeneous cell sizes and densities of the cells to be separated. In contrast, the use of focused acoustic energy is a continuous 'pushing' acoustic wave that separates cells based on differences in target surface. As a result, CTCs can be separated from WBCs and then used in later analysis.

In another illustrative application, separation of viral particles in whole blood, urine, synovial fluid, cerebrospinal fluid (CSF), etc. is important for diagnostics. Using focused acoustic energy as described herein has advantages over simple centrifugation to separate host cells and debris from virus particles because centrifugation—like filtration and other means of physical separation—suffer from viral particles being captured in the cell debris and being co-precipitated/co-eliminated. Focused acoustic energy-based separation in a continuous flow of sample through a separation chamber can be used to dislodge virus particles from host cells and cell debris followed by acoustic separation of cells from viral particles.

In yet another application, bacterial and fungal cells in a whole blood sample may be separated for use in analysis. For example, the detection and identification of microorganisms in whole blood can be useful for diagnosing the cause of disease in sepsis patients. As the current state-of-the-art sepsis assays are based on blood culture, the outcome of such analysis is largely dependent on the growth and proliferation of sepsis-causing organisms in the blood culturing media. However, several microorganisms are notoriously slow growers (certain bacteria species) or do not grow at all (e.g., *Candida glabrata* and many other fungi but also bacteria). This results in high risk for the sepsis patient as the treatment can be purely symptomatic (choosing regimens empirically) until a positive culture and organism identification is made. Molecular diagnostic sepsis assays are slowly being developed but all suffer from the same problem, i.e., the sheer overpowering ratio of host blood cell DNA or RNA to those of bacterial or fungal DNA. Sepsis can be caused by as low as 1 to 5 CFU of bacteria or fungi per ml of blood. Thus, it is of great importance to greatly enrich bacterial/fungal cells in as much as 10 ml of whole blood. One reason to do this is to reduce the background DNA from host WBCs which greatly impacts sensitivity and accuracy of downstream diagnostic assays such as qPCR, etc. For example, 1 ml of human blood contains on average 4 to 10 million white blood cells. This translates into 26 to 66 micrograms of human DNA that can theoretically be isolated from 1 ml of whole blood. In contrast, sepsis patients may contain less than 5 bacterial or fungal cells per ml of blood. Thus the ratio of host DNA to bacterial or fungal DNA is staggering and as high as 1 million or more.

An illustrative focus acoustic-based separation process for enriching sepsis-causing bacteria or fungi may include the following:

A patient's whole blood is collected into an EDTA (purple top) blood collection tube (BCT) having a volume of 6-20 ml per patient.

Red blood cells are hemolysed by passing the sample through a focused acoustic energy field at such energy that lyses the RBCs but leaves bacterial, fungal and white blood cells intact. This acoustic energy treatment may be done in a treatment chamber separate from a separation chamber. Note, that red blood cells can also be lysed chemically (detergent based by adding for example anionic, amphoteric or neutral detergents) or osmotically (by adding salt such as ammonium chloride).

The resulting sample mixture is then treated with focused acoustic energy, e.g., in a separation chamber or elsewhere, to dislodge membranes associated bacteria or fungal cells from white blood cells or cell debris. The acoustic energy is arranged such that bacterial cells (most importantly gram-negative bacteria) or WBCs are not lysed. This is important to avoid loss of target DNA or contamination of target DNA with host cell DNA.

The mixture is then passed through an acoustic separation chamber like that described above to separate white blood cells from smaller bacterial and fungal cells. For example, WBCs will generally exit a first outlet, and bacteria and fungi will exit via a second outlet of a separation chamber like that above.

After separation from WBCs, the bacteria and fungi are treated with high energy focused acoustic energy to lyse and release the nucleic acids. This treatment may be done in a chamber separate from a separation chamber. The released nucleic acids can then be purified by conventional methods such as reverse phase based bind and release (column or magnetic beads etc.) for analysis.

Figure 9:
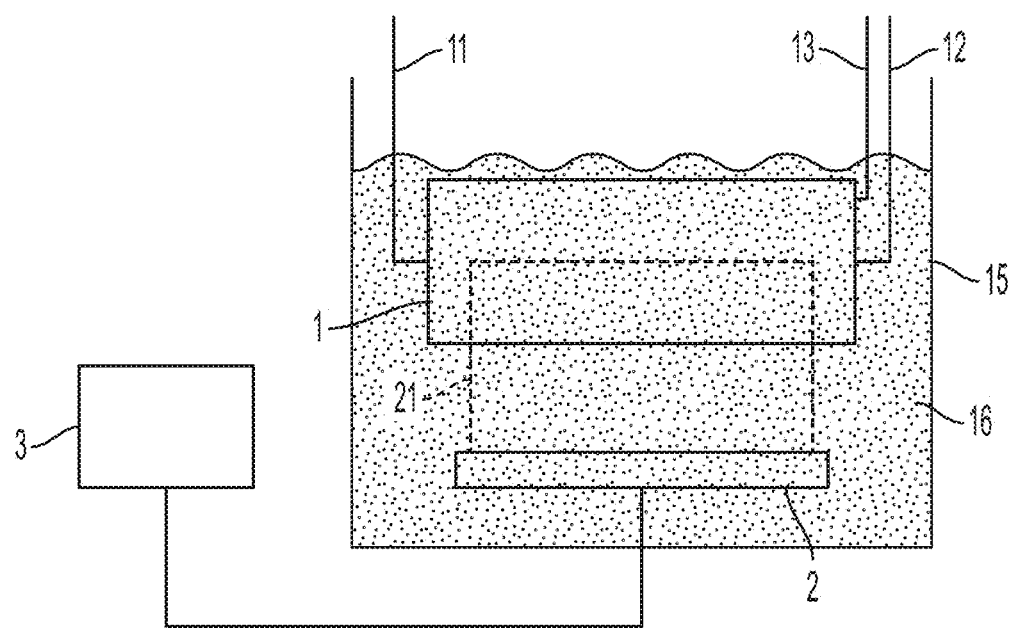
FIG. 9 is a schematic diagram of an acoustic energy system in an illustrative embodiment.

FIG. 9 shows a schematic block diagram of an acoustic energy system that may be used to provide focused acoustic treatment to a mixture in a chamber 1. "Sonic energy" or "acoustic energy" as used herein is intended to encompass such terms as acoustic waves, acoustic pulses, ultrasonic energy, ultrasonic waves, ultrasound, shock waves, sound energy, sound waves, sonic pulses, pulses, waves, or any other grammatical form of these terms, as well as any other type of energy that has similar characteristics to sonic energy. In this illustrative embodiment, the acoustic energy system includes an acoustic energy source 2 with an acoustic transducer (e.g., including one or more piezoelectric elements) that is capable of generating an acoustic field (e.g., at a focal zone 21) suitable to cause movement of cells in a chamber 1. (Although FIG. 9 shows the chamber 1 oriented for horizontal flow through the chamber 1, the chamber 1 may be oriented for vertical flow as shown in FIGS. 6 and 8 or for other inclined flow.) The mixture in the chamber 1 may include "solid" particles, such as cells, or other material, such as DNA or other nucleic acid material, one or more enzymes, etc. and/or liquid, such as liquid reagents, water, a crowding agent, etc. The chamber 1 may be supported by a holder (not shown in FIG. 9). Although a holder is not necessarily required, the holder may interface with a control circuit 3 so that the chamber 1 and mixture in the chamber 1 are positioned in a desired location relative to an acoustic field, for example, at least partially within a focal zone 21 of acoustic energy. The holder may be arranged to support the chamber 1 in a single location, or may be arranged to move the chamber 1, e.g., using a robotic system, movable stage or other drive system. In this embodiment, the chamber 1 is a cylindrical polymer tube having an internal volume of 200 milliliters to 1 liter, but it should be understood that the chamber 1 may have other suitable shapes, sizes (including volume), materials, or other features, as discussed above. The chamber 1 may be formed of glass, plastic, metal, composites, and/or any suitable combinations of materials, and formed by any suitable process, such as molding, machining, stamping, and/or a combination of processes. In some embodiments, the chamber 1 is made of a material and construction so as to be transparent or nearly transparent to acoustic energy.

As can be seen in FIG. 9, a container 15 may contain the acoustic transducer of the acoustic energy source 2, the chamber 1 as well as a coupling medium 16. The container 15 may take any suitable size, shape or other configuration, and may be made of any suitable material or combination of materials (such as metal, plastic, composites, etc.). In this illustrative embodiment, the container 15 has a jar- or can-like configuration with an opening arranged to permit access to an internal volume of the container 15. The container 15 may be arranged to hold any suitable coupling medium 16, such as water or another liquid, gas (e.g., air, inert gas), gel (e.g., silicone), solid (e.g., elastomeric material), semi-solid, and/or a combination of such components, which transmits acoustic energy from the transducer to the chamber 1. (Of course, a container 15 may not be required if the coupling medium 16 is a solid or semi-solid, e.g., the container 15 may be integrated with the coupling medium 16 itself.) The acoustic energy source 2 and the coupling medium 16 (such as water or other liquid) may be positioned in the container 15, e.g., with the acoustic energy source 2 near a bottom of the container 15, e.g., for horizontal flow chambers, or along a sidewall of the container 15 for vertical flow chambers 1. The chamber 1 can be partially or completely submerged in the coupling medium 16, and the coupling medium 16 may function as both an acoustic coupling medium, e.g., to transmit acoustic energy from the acoustic energy source 2 to the chamber 1, as well as a thermal coupling medium, e.g., to accept heat energy from the chamber 1.

Under the control of the control circuit 3 (described in more detail below), the acoustic transducer may produce acoustic energy within a frequency range of between about 100 kilohertz and about 100 megahertz such that the focal zone 21 has a width of about 2 centimeters or less. The focal zone 21 of the acoustic energy may be any suitable shape, such as spherical, ellipsoidal, rod-shaped, or column-shaped, for example, and be positioned in the chamber 1. The focal zone 21 may be larger than the chamber volume, or may be smaller than the chamber volume, as shown in FIGS. 1 and 3 for example. U.S. Pat. Nos. 6,948,843 and 6,719,449 are incorporated by reference herein for details regarding the construction and operation of an acoustic transducer and its control. The focal zone may be stationary relative to the sample, or it may move relative to the sample.

In some embodiments, the transducer can be formed of a piezoelectric material, such as a piezoelectric ceramic. The ceramic may be fabricated as a "dome", which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing or undamped to increase power output. The response may be linear if not overdriven. The high-energy focus zone 21 of one of these domes is typically cigar-shaped. At 1 MHz, the focal zone 21 is about 6 cm long and about 2 cm wide for a 20 cm dome, or about 15 mm long and about 3 mm wide for a 10 cm dome. The peak positive pressure obtained from such systems at the focal zone 21 is about 1 MPa (mega Pascal) to about 10 MPa pressure, or about 150 PSI (pounds per square inch) to about 1500 PSI, depending on the driving voltage. The focal zone 21, defined as having an acoustic intensity within about 6 dB of the peak acoustic intensity, is formed around the geometric focal point. It is also possible to generate a line-shaped focal zone, e.g., that spans the length of the chamber as discussed above.

To control an acoustic transducer, the system control circuit 3 may provide control signals to a load current control circuit, which controls a load current in a winding of a transformer. Based on the load current, the transformer may output a drive signal to a matching network, which is coupled to the acoustic transducer and provides suitable signals for the transducer to produce desired acoustic energy. Moreover, the system control circuit 3 may control various other acoustic treatment system functions, such as positioning of the chamber 1 and/or acoustic transducer (e.g., by controlling the holder to suitably move and hold the chamber 1 in a desired location), receiving operator input (such as commands for system operation by employing a user interface), outputting information (e.g., to a visible display screen, indicator lights, sample treatment status information in electronic data form, and so on), and others. Thus, the system control circuit 3 may include any suitable components to perform desired control, communication and/or other functions. For example, the system control circuit 3 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the chamber 1 or other components, position sensors to indicate positions of the acoustic transducer and/or the chamber 1, turbidity or other measurement of cell concentrations in a flow into or out of the chamber 1, and so on), user data input devices (such as buttons, dials, knobs, a keyboard, a touch screen or other), information display devices (such as an LCD display, indicator lights, a printer, etc.), and/or other components for providing desired input/output and control functions. Also, the control circuit 3 may include one or more components to detect and control a temperature of the coupling medium 16, such as a refrigeration system to chill the coupling medium 16, a degassing system to remove dissolved gas from the coupling medium 16, etc. Circulating the coupling medium 16 may allow the control circuit 3 to remove portions of the coupling medium 16 from the container 15 for processing, such as degassing, chilling, replacement, addition of compounds, etc.

Although not necessarily critical to employing aspects of the invention, in some embodiments, sample treatment control may include a feedback loop for regulating at least one of acoustic energy location, frequency, pattern, intensity, duration, and/or absorbed dose of the acoustic energy to achieve the desired result of acoustic treatment. One or more sensors may be employed by the control circuit 3 to sense parameters of the acoustic energy emitted by the transducer and/or of the mixture, and the control circuit 3 may adjust parameters of the acoustic energy and/or of the mixture (such as flow rate, concentration, etc.) accordingly. Thus, control of the acoustic energy source may be performed by a system control unit using a feedback control mechanism so that any of accuracy, reproducibility, speed of processing, control of temperature, provision of uniformity of exposure to sonic pulses, sensing of degree of completion of processing, monitoring of cavitation, and control of beam properties (including intensity, frequency, degree of focusing, wave train pattern, and position), can enhance performance of the treatment system. A variety of sensors or sensed properties may be used by the control circuit for providing input for feedback control. These properties can include sensing of temperature, cell concentration or other characteristic of the mixture; sonic beam intensity; pressure; coupling medium properties including temperature, salinity, and polarity; chamber position; conductivity, impedance, inductance, and/or the magnetic equivalents of these properties, and optical or visual properties of the mixture. These optical properties, which may be detected by a sensor typically in the visible, IR, and UV ranges, may include apparent color, emission, absorption, fluorescence, phosphorescence, scattering, particle size, laser/Doppler fluid and particle velocities, and effective viscosity. Mixture integrity and/or comminution can be sensed with a pattern analysis of an optical signal from the sensor. Particle size, solubility level, physical uniformity and the form of particles could all be measured using instrumentation either fully standalone sampling of the fluid and providing a feedback signal, or integrated directly with the focused acoustical system via measurement interface points such as an optical window. Any sensed property or combination thereof can serve as input into a control system. The feedback can be used to control any output of the system, for example beam properties, flow in the chamber, treatment duration, and losses of energy at boundaries and in transit via reflection, dispersion, diffraction, absorption, dephasing and detuning.

The desired result of acoustic treatment, which may be achieved or enhanced by use of ultrasonic wavetrains, can be, without limitation, moving cells in the chamber to aid in separating cells from a mixture, but also heating the mixture, cooling the mixture, fluidizing the mixture, micronizing the mixture, mixing the mixture, stirring the mixture, disrupting the mixture, permeabilizing a component of the mixture, forming a nanoemulsion or nano formulation, enhancing a reaction in the mixture, solubilizing, sterilizing the mixture, lysing, extracting, comminuting, catalyzing, and/or selectively degrading at least a portion of a mixture. In embodiments specifically discussed herein, specialized mixing of the mixture is particularly effective in enhancing ligation reactions. Sonic waves may also enhance filtration, fluid flow in conduits, and fluidization of suspensions. Processes in accordance with the present disclosure may be synthetic, analytic, or simply facilitative of other processes such as stirring.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

The invention claimed is:

1. A method of separating cells from a liquid mixture, comprising:
    providing a plurality of whole cells in a mixture containing liquid into a chamber via an inlet of the chamber;
    transmitting focused acoustic energy into the chamber to create a focal zone of acoustic energy in the chamber so as to expose the plurality of whole cells in the mixture to acoustic energy at the focal zone, the chamber being absent of any standing acoustic waves;
    moving the plurality of whole cells in the chamber using at least in part the focused acoustic energy so the plurality of whole cells exit the chamber via a first outlet rather than a second outlet;
    removing the plurality of whole cells from the chamber via the first outlet; and
    removing liquid of the mixture from the chamber via the second outlet.

2. The method of claim 1, wherein the chamber includes a filter that flowwise separates a first portion of the chamber that is in fluid communication with the inlet and the first outlet and a second portion of the chamber that is in fluid communication with the second outlet, the filter being arranged such that liquid that enters the chamber at the inlet must pass through the filter to exit the chamber via the second outlet.

3. The method of claim 2, wherein the filter is arranged such that each whole cell in the plurality of whole cells is too large to pass through the filter.

4. The method of claim 2, wherein the filter has an area of at least 100 to 2000 square mm.

5. The method of claim 2, wherein the focused acoustic energy moves the plurality of whole cells away from the filter.

6. The method of claim 2, wherein the chamber includes a first end where the inlet is located that is opposite a second end where the first and second outlets are located, and wherein the filter extends in a direction from the first end to the second end.

7. The method of claim 6, wherein the focused acoustic energy is transmitted into the chamber between the first and second ends so that a line-shaped focal zone is arranged in a direction from the first end to the second end.

8. The method of claim 7, wherein the line-shaped focal zone is located above the filter.

9. The method of claim 7, wherein the line-shaped focal zone has a length of 75 mm.

10. The method of claim 1, wherein the focused acoustic energy has a frequency of 0.25 to 2.5 MHz.

11. The method of claim 1, wherein the plurality of whole cells are viable when introduced into the chamber via the inlet and are viable after being removed from the chamber via the first outlet.

12. The method of claim 1, wherein the plurality of whole cells have a concentration of near zero to 50% in the mixture at the inlet.

13. The method of claim 1, wherein the mixture is introduced into the chamber at a flow rate of 1 milliliter per minute to 1000 milliliters per minute.

14. The method of claim 1, wherein the focal zone has a line-shape, and the plurality of whole cells move within the chamber in a direction along the line-shaped focal zone.

15. The method of claim 1, wherein the inlet is located at a first end of the chamber and the first and second outlets are arranged at a second end of the chamber opposite the first end.

16. The method of claim 15, wherein flow from the inlet to the first and second outlets is horizontal, and the first outlet is positioned below the second outlet.

17. The method of claim 15, wherein flow from the inlet to the first and second outlets is vertical and the inlet is located above the first and second outlets.

18. The method of claim 15, wherein the focused acoustic energy enters the chamber along a first side of the chamber, and the first outlet is arranged nearer the first side than the second outlet.

19. The method of claim 1, wherein the inlet and the first outlet are located at a first end of the chamber and the second outlet is arranged at a second end of the chamber opposite the first end.

20. The method of claim 19, wherein flow from the inlet to the second outlet is vertical and the inlet is located below the second outlet.

21. The method of claim 19, wherein the focused acoustic energy enters the chamber along a first side of the chamber, and the first outlet is arranged nearer the first side than the inlet.

22. The method of claim 19, wherein the plurality of whole cells are moved at least in part to the first outlet by gravity.

* * * * *